(12) United States Patent
Nishii et al.

(10) Patent No.: US 6,764,655 B1
(45) Date of Patent: Jul. 20, 2004

(54) PHOTOCATALYST FILTER FOR A LIGHT LEAKAGE TYPE

(75) Inventors: Yoshikazu Nishii, Tokyo (JP); Jumpei Hama, Tokyo (JP); Soji Arai, Saitama (JP)

(73) Assignees: Hoya Corporation, Tokyo (JP); Hoya Candeo Optronics Corporation, Tokyo (JP)

( * ) Notice: Subject to any disclaimer, the term of this patent is extended or adjusted under 35 U.S.C. 154(b) by 597 days.

(21) Appl. No.: 09/606,678

(22) Filed: Jun. 30, 2000

(30) Foreign Application Priority Data

Jun. 30, 1999 (JP) .......................................... 11-186740

(51) Int. Cl.[7] ................................................. A61L 2/00
(52) U.S. Cl. .................. 422/122; 210/500.26; 422/121; 422/186; 422/186.3; 422/22; 422/24
(58) Field of Search ................ 422/121, 122, 422/186, 186.3, 22, 24; 210/497.3, 500.26

(56) References Cited

U.S. PATENT DOCUMENTS

| | | | | |
|---|---|---|---|---|
| 5,875,384 A | * | 2/1999 | Peill et al. ................ | 422/186.3 |
| 6,108,476 A | * | 8/2000 | Iimura ......................... | 385/128 |
| 6,468,428 B1 | * | 10/2002 | Nishii et al. ............. | 210/497.3 |
| 6,501,893 B1 | * | 12/2002 | Iimura ........................ | 385/128 |

* cited by examiner

*Primary Examiner*—Krisanne Thornton
(74) *Attorney, Agent, or Firm*—Sughrue Mion, PLLC

(57) ABSTRACT

Light-leakage type photocatalyst fibers (10) are bundled together to form a filter assembly having an enormous number of minute gaps which provide fluid communication paths in a longitudinal direction of the photocatalyst fibers. Light is incident to each of the photocatalyst fibers constituting the filter assembly while an object fluid to be processed is introduced through an end face of the filter assembly to pass through the gaps among the photocatalyst fibers in the longitudinal direction.

6 Claims, 9 Drawing Sheets

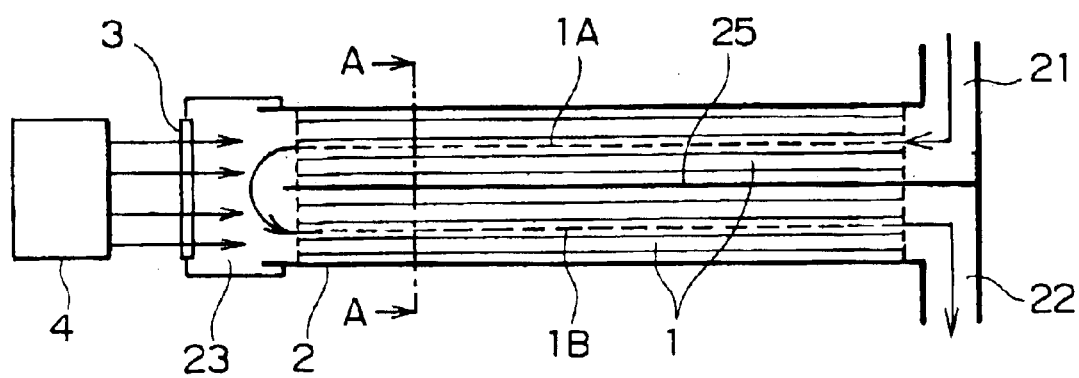
FIG. 3A
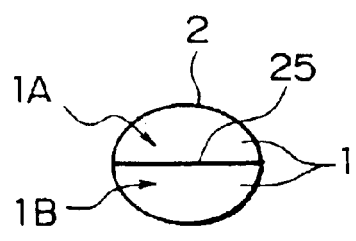 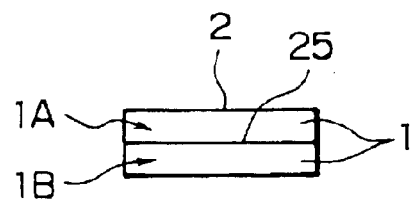
FIG. 3B          FIG. 3C

PHOTOCATALYST FILTER FOR A LIGHT LEAKAGE TYPE

BACKGROUND OF THE INVENTION

The present invention relates to a photocatalyst filter which uses a photocatalyst fiber of a light-leakage type and which will be called a light-leakage type photocatalyst filter hereinafter.

It is a recent trend that various problems have been presented about environmental pollution, such as air pollution. As regards the air pollution, it has been required for health to remove toxic substances, such as benzene, acetaldehyde, and the like from the air. To this end, various sorts of filters have been developed and sold but no proposals have been made yet which have sufficient characteristics.

The instant inventors have already proposed and filed a photocatalyst filter, namely, a photochemical catalysis filter which uses a bundle of photocatalyst fibers for removing the toxic substances from the air. With this structure, ultraviolet rays travel along the photocatalyst fibers and partially and gradually leak from the photocatalyst fibers to photochemically react with the toxic substances. Such photochemical reaction makes it possible to considerably remove the toxic substances, such as acetaldehyde. This type of the photocatalyst filter may be referred to as a light-leakage photocatalyst filter because light leakage is utilized in the photocatalyst filter.

More specifically, a light-leakage type photocatalyst filter proposed by the inventors comprises a bundle of photocatalyst fibers each of which has a fiber core portion formed by a photoconductor and a surface layer containing a photocatalyst, such as titanium oxide, and serving as a photocatalyst layer. The photocatalyst layer is activated by light or ultraviolet ray introduced into the fiber. The light travels along the photocatalyst fibers while partially leaking therefrom. Thus, the light-leakage type photocatalyst fiber exhibits a catalytic action. As mentioned before, the light-leakage type photocatalyst filter can be formed by bundling a plurality of light-leakage type photocatalyst fibers.

FIG. 1 shows an example of the light-leakage type photocatalytic filter.

Referring to FIG. 1, the light-leakage type photocatalyst filter generally comprises a light-leakage type photocatalyst fiber bundle 101, a casing 102, a light introducing window 103, and a light source 104.

The casing 102 is provided with an inflow port 121 and an outflow port 122 for an object fluid (for example, an air) to be processed, and has a structure such that the photocatalyst fiber bundle 101 is interposed between the inlet port 121 and the outlet port 122. The light introducing window 103 is formed at a part of the casing 102 to introduce the light from the light source 104 into the photocatalyst fiber bundle 101.

In the filter shown in FIG. 1, the object fluid passes through the filter across the light-leakage type photocatalyst fiber bundle 101. Thus, the object fluid is introduced into the casing 102 through the inflow port 121 and crosses the fiber bundle 101 during passage of the filter. During passage, the object fluid is filtered by both a mechanical filtering action of the fiber bundle 101 and a photochemical catalytic action of the photocatalyst fibers. As a result, the object substantially free from the toxic substance is discharged from the outflow port 122. However, it has been revealed by the present inventors that the conventional filter described above is disadvantageous in the following respects.

In the filter shown in FIG. 1, the object fluid crosses the photocatalyst fiber bundle 101 within the filter. It is therefore difficult to assure or lengthen a traveling distance (path length) within the filter, i.e., a so-called effective filter length. In addition, a passageway resistance across the fiber bundle 101 becomes undesirably large. This results in an increase of a pressure loss in the filter.

As a consequence, the efficiency of use of the photocatalyst fibers is low and thus a sufficient filtering capacity cannot be obtained as compared with the numbers of necessary photocatalyst fibers.

SUMMARY OF THE INVENTION

It is therefore an object of the present invention is to provide a light-leakage type photocatalyst filter capable of simultaneously satisfying contradictory demands for sufficiently lengthening an effective filter length, for reducing a pressure loss in the filter, and for increasing a filtering capacity by improving the efficiency of use of photocatalyst fibers.

According to a first aspect of this invention, there is provided a light-leakage type photocatalyst filter comprising a filter assembly including a plurality of photocatalyst fibers each of which is composed of a fiber-shaped base member of a photoconductor and a surface layer containing a photocatalyst and which are bundled together into a photocatalyst fiber bundle with a gap left between every adjacent ones of said photocatalyst fibers; light introducing means for introducing the light into each of said photocatalyst fibers forming the filter assembly; and fluid introducing means for introducing an object fluid to be processed into the filter assembly to make the fluid pass through the gap between the adjacent ones of the photocatalyst fibers in a longitudinal direction of the photocatalyst fibers.

According to a second aspect of this invention, the light-leakage type photocatalyst filter may have a reservoir formed in front of an end face of the filter assembly.

According to a third aspect of this invention, the photocatalyst fibers may be bundled together with granular spacers interposed between every adjacent ones of the fibers.

According to a fourth aspect of this invention, the filter assembly may be divided by a partition wall disposed along the longitudinal direction of the photocatalyst fibers to form a plurality of filter paths and to form a cascade channel in which the fluid object successively passes through the filter paths.

According to a fifth aspect of this invention, the photocatalyst fiber bundle may have a dense portion and a sparse portion formed at a part and another part in the longitudinal direction where the fibers are densely and sparsely arranged, respectively. The dense portion serves as the filter assembly while the sparse portion serves as a fluid introducing section communicating with an end face of the filter assembly.

According to a sixth aspect of this invention, the photocatalyst fiber bundle forming the filter assembly is arranged so that their end faces are inclined with respect to the longitudinal direction of the fiber bundle.

According to a seventh aspect of this invention, a traveling direction of the object fluid within the photocatalyst fiber bundle forming the filter assembly may be perpendicular to a light introducing direction of introducing the light into each photocatalyst fiber.

According to an eighth aspect of this invention, a traveling direction of the object fluid within the photocatalyst fiber bundle forming the filter assembly may be coincident with a light introducing direction of introducing the light into each photocatalyst fiber.

According to a ninth aspect of this invention, the light-leakage type photocatalyst filter may have a fluorescent surface formed on a light introduction end face of each of the photocatalyst fibers to perform secondary emission.

According to a tenth aspect of this invention, the light-leakage type photocatalyst filter may have an antireflection layer formed on an end face of each of the photocatalyst fibers on a light introduction end.

According to an eleventh aspect of this invention, there is provided a light-leakage type photoctalyst fileter comprising a filter assembly including a plurality of photocatalyst fibers each of which is composed of a fiber-shaped base member of a photoconductor and a surface layer containing a photocatalystand which are bundled together into a photocatalyst fiber bundle with a gap left between every adjacent ones of said photoctalyst fibers, a fluid inlet/outlet pipe having inflow and outflow ports for an object fluid containing an object material to be processed by the photocatalyst; and a light source for introducing the light into the photoconductor, wherein the filter assembly is disposed in the fluid inlet/outlet pipe so that a flowing direction of the object fluid is substantially coincident with a longitudinal direction of the fiber-shaped base members constituting the filter assembly while the light source is disposed so as to introduce the light into the fiber-shaped base members.

According to the present invention, the object fluid can be made to pass through the photocatalyst fiber bundle in the longitudinal direction thereof and the flow rate distribution of the object fluid can be uniformly distributed in the fiber bundle.

As a result, it is possible to achieve the object, i.e., to simultaneously satisfy the contradictory demands for assuring an effective filter length which is sufficiently long, for reducing a pressure loss in the filter, and for increasing a filter capacity by improving the efficiency of use of the photocatalyst fibers.

BRIEF DESCRIPTION OF THE DRAWINGS

FIG. 3A shows a light-leakage type photocatalyst filter according to a second embodiment of this invention;

FIGS. 3B and 3C are sectional views taken along a line III—III in FIG. 3A for describing different sections of a fiber bundle;

DESCRIPTION OF THE PREFERRED EMBODIMENTS

Figure 1:
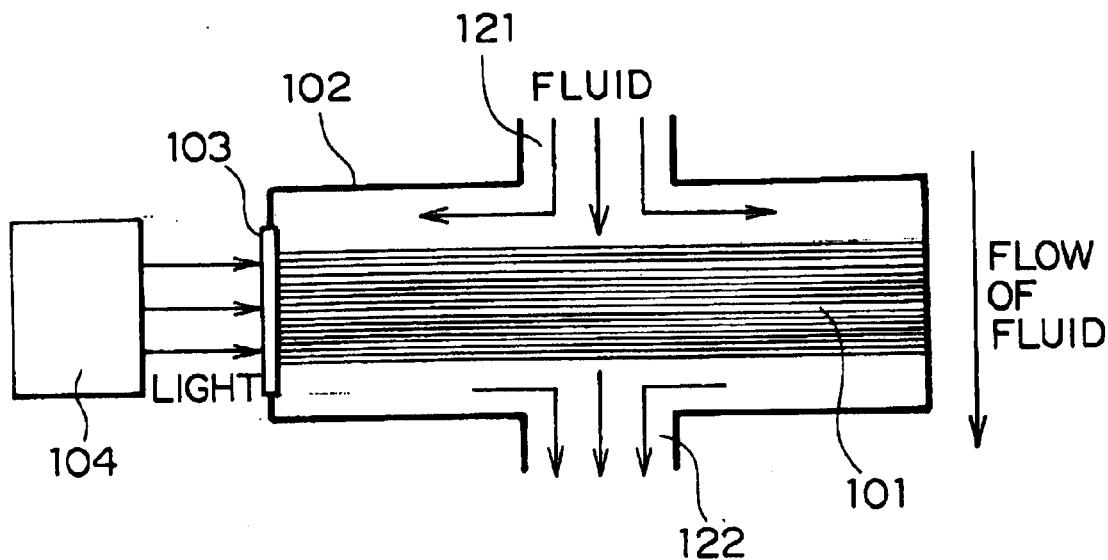
FIG. 1 shows a conventional light-leakage type photo catalyst filter.

Now, several preferred embodiments of the present invention will be described with reference to the accompanying drawings.

Similar parts are designated by like reference numerals in the following drawings.

Figure 2A:
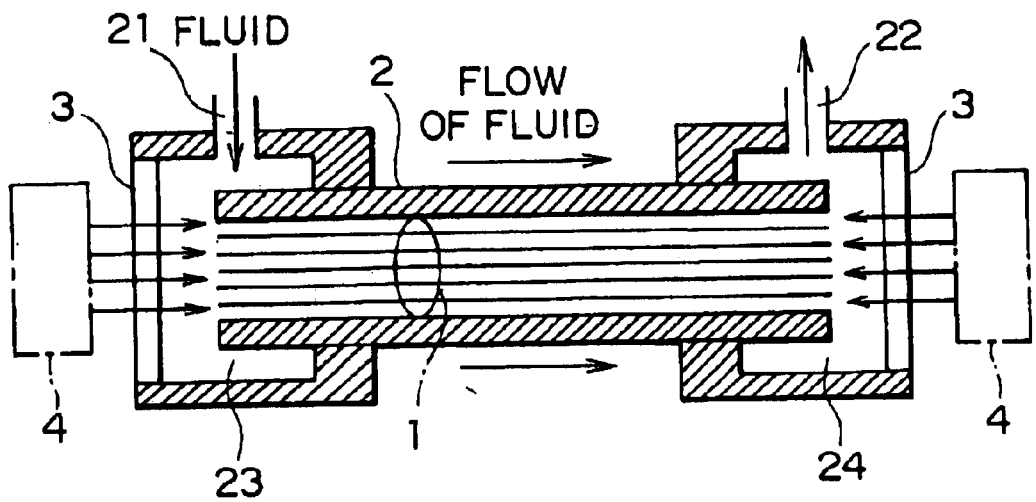
FIGS. 2A, 2B, and 2C show a light-leakage type photocatalyst filter according to a first embodiment of the present invention, FIG. 2A being a schematic vertical sectional view of an overall structure, FIG. 2B being a partially enlarged sectional view, FIG. 2C being a side sectional view.
Figure 2B:
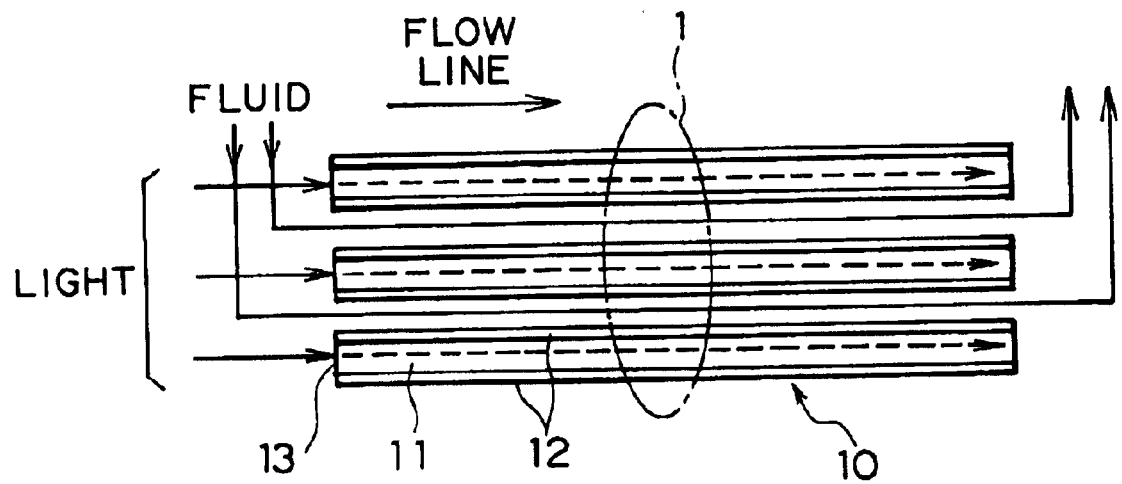
Figure 2C:
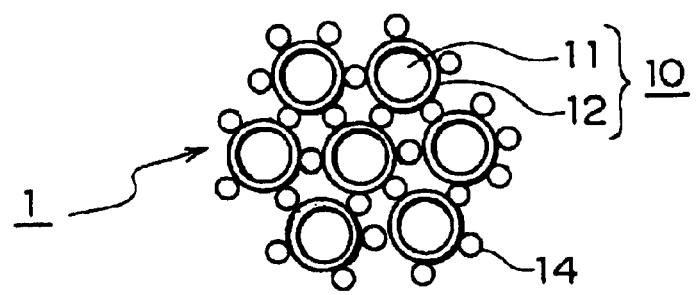

Referring to FIGS. 2A–2C, a light-leakage type photocatalyst filter according to a first embodiment of the present invention generally comprises a light-leakage type photocatalyst fiber bundle 1, a casing 2, a pair of light introducing windows 3, and a pair of light sources 4.

The photocatalyst fiber bundle 1 is inserted into and tightly fitted to an intermediate cylindrical portion of the casing 2 and hermetically sealed to be isolated from the outside except both ends thereof. With this structure, the photocatalyst fiber bundle 1 forms a filter assembly which has a large number of photocatalyst fibers of a light leakage type (may be called light-leakage type photocatalyst fibers or may be simply called fibers) with an enormous number of minute gaps left among the fibers along the longitudinal direction of the fibers in a manner to be described later. The object fluid, which includes a toxic substance, is caused to flow through the gaps in the longitudinal direction of the fibers. The fibers in the photocatalyst fiber bundle 1 are about 10,000 in number and are 125 $\mu$m in diameter and 200 mm in length.

Each of the light introducing windows 3 is composed of a transparent material, such as a glass, transparent to ultraviolet rays or beams. The light introducing windows 3 are located or positioned on both ends of the casing 2 to introduce light beams from the light sources 4 into the end faces of the fiber bundle 1. The light introducing windows 3 serve as light introducing means for introducing the light beams into the photocatalyst fibers of the photocatalyst fiber bundle 1.

The casing 2 cooperates with an inflow port 21 and an outflow port 22 formed in the vicinity of both ends. The inflow and the outflow ports 21 and 22 introduce an object fluid to be processed to one end face of the photocatalyst fiber bundle 1 and discharge a processed fluid from the other end face of the photocatalyst fiber bundle 1, respectively. A pair of reservoirs 23 and 24 are formed between the inflow port 21 and one end face of the fiber bundle 1 and between the outflow port 22 and the other end face of the fiber bundle 1, respectively, to receive or keep the object fluid.

The object fluid is introduced through the inflow port 21 into the reservoir 23, and is supplied from the reservoir 23 to the one end face of the photocatalyst fiber bundle 1 to pass through the fiber bundle 1 in the longitudinal direction of the fibers. During passage through the fiber bundle 1, the object fluid is processed or effectively filtered from the toxic substance. After a passage through the fiber bundle 1, the fluid is guided to the outflow port 22 from the reservoir 24 located on the side of the other end face of the fiber bundle 1.

Thus, the object fluid is allowed to pass through the fiber bundle 1 in the longitudinal direction thereof as described above. Therefore, it is possible to sufficiently assure, namely, lengthen a traveling distance (path length) within the filter, i.e., an effective filter length. In addition, a pressure loss in the filter can be suppressed by decreasing a passageway resistance. Further, by introducing the object fluid from the end face of the photocatalyst fiber bundle 1, it is possible to achieve uniform distribution of the flow rate within the photocatalyst fiber bundle 1.

With the above-mentioned structure, it is possible to achieve the object of this invention, i.e., to simultaneously satisfy the contradictory demands for assuring an effective filter length which is sufficiently long, for reducing a pressure loss in the filter, and for increasing a filter capacity by improving the efficiency of use of the photocatalyst fibers.

The reservoirs 23 and 24 act to obtain uniform pressure distribution of the object fluid on the both end faces of the photocatalyst fiber bundle 1 to thereby achieve more uniform flow rate distribution in the photocatalyst fiber bundle 1. In this case, the reservoir 23 on the inlet side acts to achieve uniform distribution of a positive pressure applied to one end face of the fiber bundle 1. On the other hand, the reservoir 24 on the outlet side acts to achieve uniform distribution of a negative pressure applied to the other end face of the fiber bundle 1.

As shown in FIG. 2B, the photocatalyst fiber bundle 1 forms the filter assembly obtained by bundling the photocatalyst fibers 10 and keeps an enormous number of the minute gaps for providing passages of the object fluid in the longitudinal direction of the fibers 10. Each of the light-leakage type photocatalyst fibers 10 comprises an optical core portion 11 and a photocatalyst layer 12, such as titanium oxide, covered on the optical core portion 11. Light rays, such as ultraviolet rays, travel along the photocatalyst fibers 10 in the longitudinal direction of the fibers while partial leakage of the light rays takes place. During the passage of the light or light rays, the photocatalyst layer 12 is activated by the light introduced into the optical fiber 11 and is caused to the light to partially leak outside of the fibers. Thus, such activation of the photocatalyst layer 12 of the catalyst fiber 10 brings about a catalytic action. The filter having the catalytic action, that is, the light-leakage type photocatalyst filter can be formed by bundling the light-leakage type photocatalyst fibers 10.

It is preferable that each of the end faces of each photocatalyst fiber 10 forms a plane exactly perpendicular to the longitudinal direction of the fiber 10 and is sufficiently polished. Furthermore, each of the end faces desirably has an antireflection layer 13 formed thereon.

The object fluid is filtered through an enormous number of the minute gaps formed among the photocatalyst fibers 10. As illustrated in FIG. 2C, granular spacers 14 are interposed between adjacent ones of the photocatalyst fibers 10. Such granular spacers 14 are formed by irregularly coating glass like beads on each fiber along the longitudinal direction and have a maximum height of 50 $\mu$m. As a result, the spacers 14 among the photocatalyst fibers 10 serve to maintain the minute gaps of 100 $\mu$m at maximum. Thus, the minute gaps 14 can reliably be formed into a size corresponding to that of the granular spacers 14. In this case, the granular spacers 14 are secured or coated onto the surfaces of the photocatalyst fibers 10 and thereafter assembled into the bundle 1 by fixing the photocatalyst fibers 10 and the spacers 14 together.

Referring to FIGS. 3A, 3B, and 3C, description will be made of a light-leakage type photocatalyst filter according to a second embodiment of this invention.

As shown in FIG. 3A, a photocatalyst fiber bundle 1, which constitutes a filter assembly in the casing 2, is divided into two parts by a partition wall 25 of a flat shape extending along the longitudinal direction of the photocatalyst fibers. As a consequence, two filter paths 1A and 1B are formed on both upward and downward sides of the partition wall 25. The object fluid is allowed to continuously pass through the two filter paths 1A and 1B which form a cascade passageway in combination. With this structure, the object fluid is made to pass through the filter assembly of the passageway that is as long as twice the fiber bundle 1. This results in a substantial increase in an effective filter length.

As shown in FIGS. 3B and 3C, the photocatalyst fiber bundles 1 illustrated in FIG. 3A may be circular and rectangular in cross section, respectively. In any event, the partition walls 25 are disposed. In the casing 2 so that the intermediate portions of the cylindrical and the prismatic shapes are divided into two parts equal in sectional area.

The single partition wall 25 is provided in the illustrated example. It is noted here that providing two or more partition walls can increase to the effective filter length three times or more.

Referring to FIGS. 4A, 4B, 4C, and 4D, description will be made of a light-leakage type photocatalyst filter according to a third embodiment of this invention.

The third embodiment is basically similar to the second embodiment except that a partition wall 26 of a cylindrical shape is located instead of the partition wall 25. In this embodiment, the fiber bundle 1 is divided by the cylindrical partition wall 26 into an outer filter path 1A and an inner filter path 1B coaxially arranged.

Figure 4A:
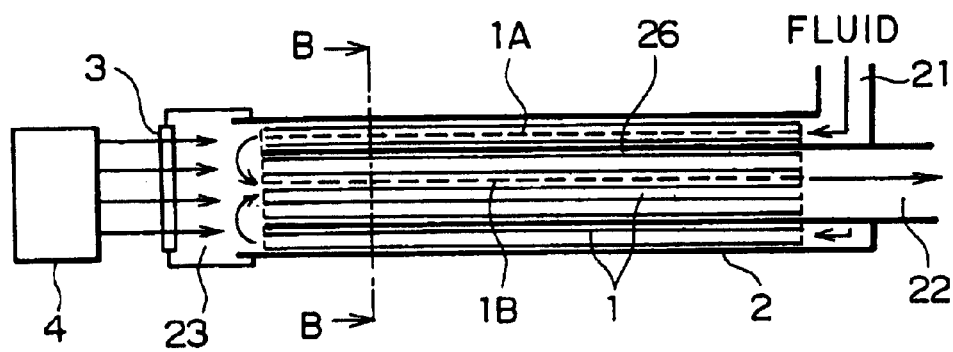
FIG. 4A shows a light-leakage type photocatalyst filter according to a third embodiment of this invention.
Figure 4B:
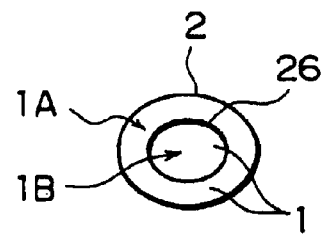
FIGS. 4B–4D are sectional views taken along a line IV—IV in FIG. 4A for describing different sections of a fiber bundle.
Figure 4C:
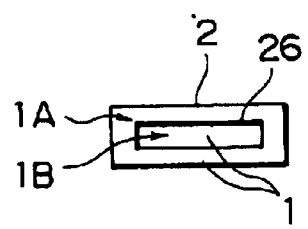
Figure 4D:
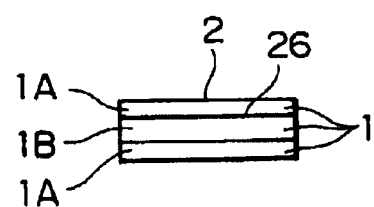

Referring to FIGS. 4B and 4C, the cylindrical partition wall 26 has a circular section and a rectangular section, respectively. Referring to FIG. 4D, the prismatic partition wall 26 of a rectangular section has both side walls aligned with those of the casing 2.

Figure 5:
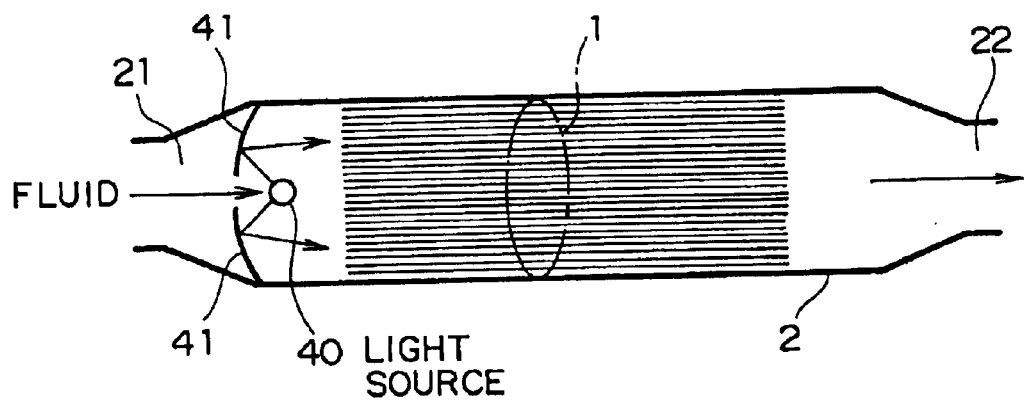
FIG. 5 is a schematic sectional view showing a light-leakage type photocatalyst filter according to a fourth embodiment of the present invention.

Referring to FIG. 5, description will be made of a light-leakage type photocatalyst filter according to a fourth embodiment of the present invention.

In the fourth embodiment shown in FIG. 5, an object fluid passing through a photocatalyst fiber bundle 1 forming a filter assembly is caused to flow in a traveling direction identical with a light introducing direction of the light introduced into each photocatalyst fiber.

As illustrated in the figure, a light source 40 which may be considered as a point light source is disposed in a casing 2. A light converging reflection mirror 41 is used so that the light emitted from the light source 40 is incident exclusively to one end face of the photocatalyst fiber bundle 1 in a direction perpendicular to the one end face. The reflection mirror 41 is provided with a hole formed at the center thereof to secure a fluid introduction path from an inflow port 21.

As described above, the traveling direction of the object fluid is identical with the light introducing direction. With this structure, the filter can be made compact and slender in its profile. In addition, piping for charging and discharging the object fluid can be simply arranged along a common axis.

Figure 6:
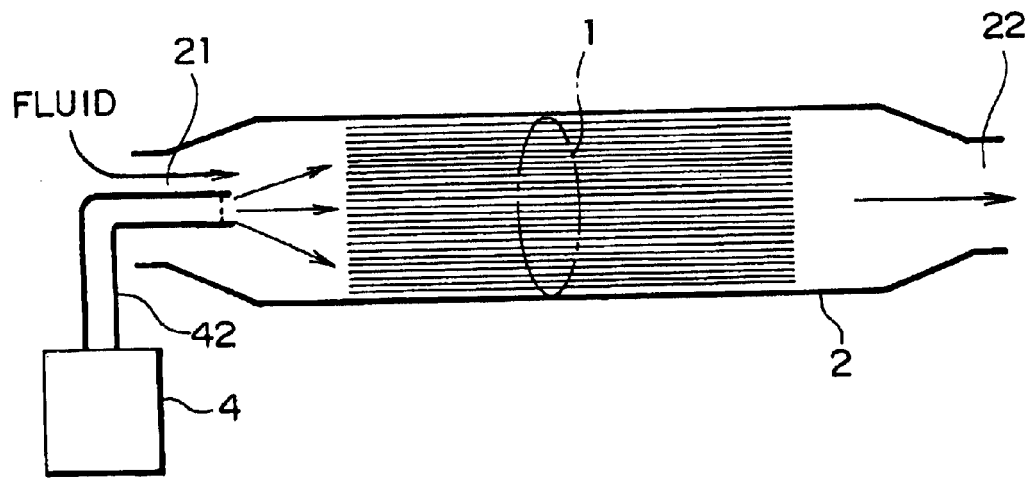
FIG. 6 is a schematic sectional view showing a light-leakage type photocatalyst filter according to a fifth embodiment of the present invention.

Referring to FIG. 6, description will be made of a light-leakage type photocatalyst filter according to a fifth embodiment of the present invention.

The fifth embodiment shown in FIG. 6 has a coaxial structure and is basically similar to the fourth embodiment shown in FIG. 5. In the fifth embodiment, however, an external light source 4 is disposed outside a casing 2 and the light from the external light source 4 is guided to one end face of a photocatalyst fiber bundle 1 in the casing 2 through a light guiding optical fiber 42. With this structure, a large sectional area can be secured at a fluid introducing path and establishes a reduction of a pressure loss therein, as compared with FIG. 5.

Figure 7A:
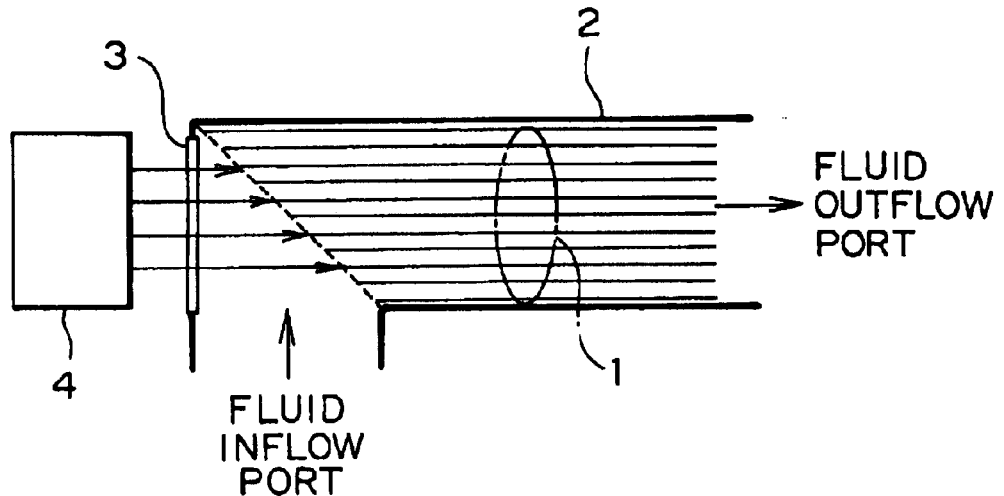
FIG. 7A is a schematic sectional view showing a modification in shape of an end face of a photocatalyst fiber bundle used in the present invention.
Figure 7B:
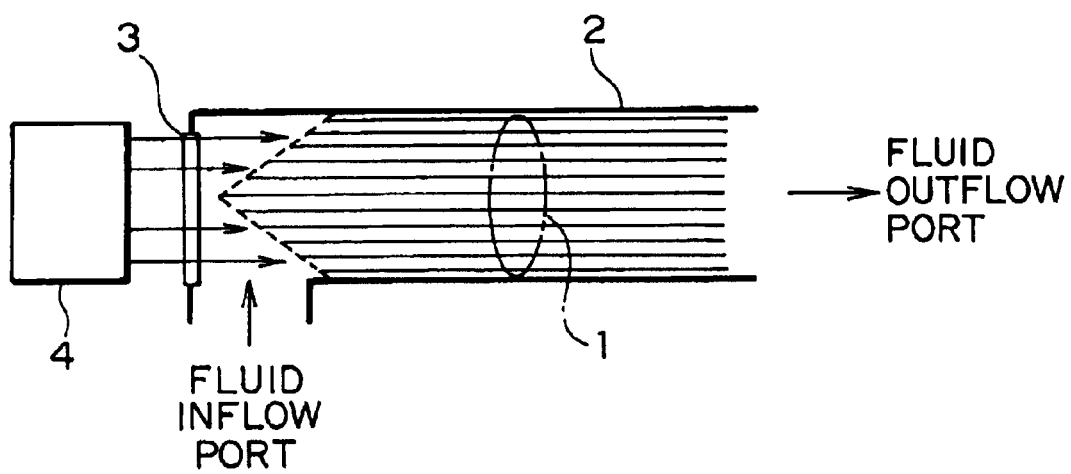
FIG. 7B is a schematic sectional view showing another modification different from that shown in FIG. 7A.

Referring to FIGS. 7A and 7B, the photocatalyst fiber bundle used in the present invention may be modified in shape of the end face of the photocatalyst fiber bundle 1.

In each of the foregoing embodiments, the end face of the photocatalyst fiber bundle 1 is flat and perpendicular to the longitudinal direction of the fibers. However, the end face of the photocatalyst fiber bundle 1 may not be perpendicular to the longitudinal direction of the fibers. It is noted here that an end face of each individual fiber is preferably perpendicular to the longitudinal direction of the fiber.

Referring to FIG. 7A, the photocatalyst fiber bundle 1, which constitutes a filter assembly, has an end face inclined at about 45° with respect to the longitudinal direction of the fiber bundle 1. With this structure, the end face of the fiber bundle 1, through which the object fluid is introduced, has a large area as compared with the end face perpendicular to the longitudinal direction. This results in an improvement in efficiency of the photocatalytic action and a reduction in pressure loss of the object fluid.

In this case, a light incident direction of the light incident onto the fiber bundle 1 intersects a fluid introducing direction of the fluid introduced at an angle of about 90°.

Referring to FIG. 7B, the photocatalyst fiber bundle 1 has an end face of a conical shape. Like in FIG. 7A, the end face of the fiber bundle 1 is increased in area so as to achieve an improvement in efficiency of the photocatalytic action and a reduction in pressure loss of the object fluid.

Figure 8A:
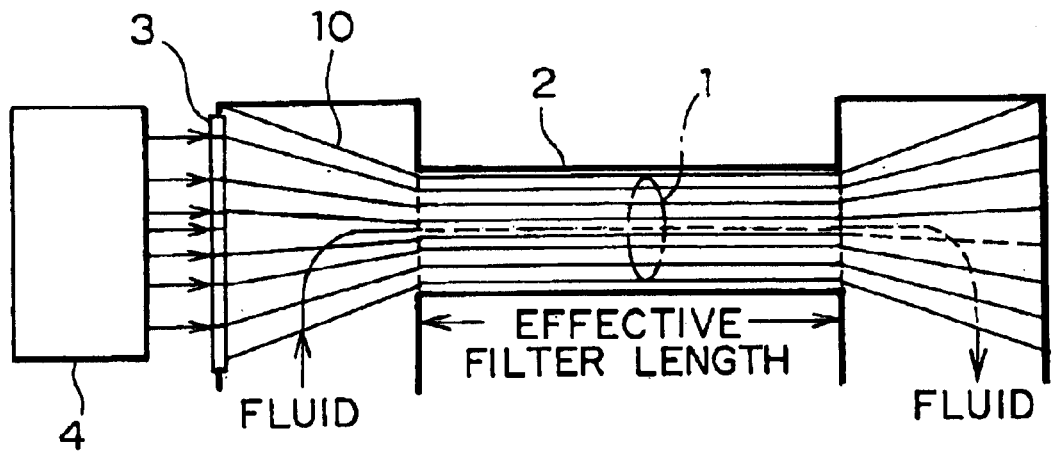
FIGS. 8A–8C are schematic sectional views showing various modifications of a filter assembly formed by photocatalyst fibers.
Figure 8B:
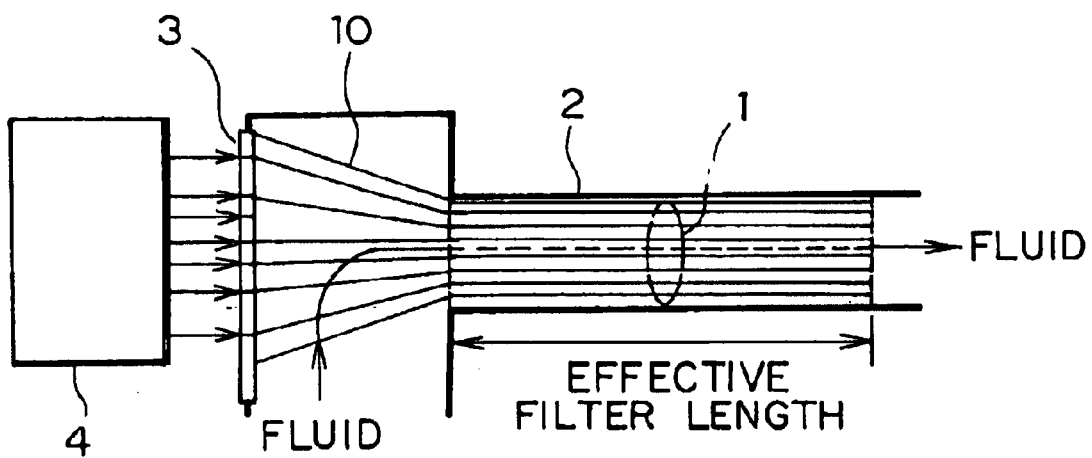
Figure 8C:
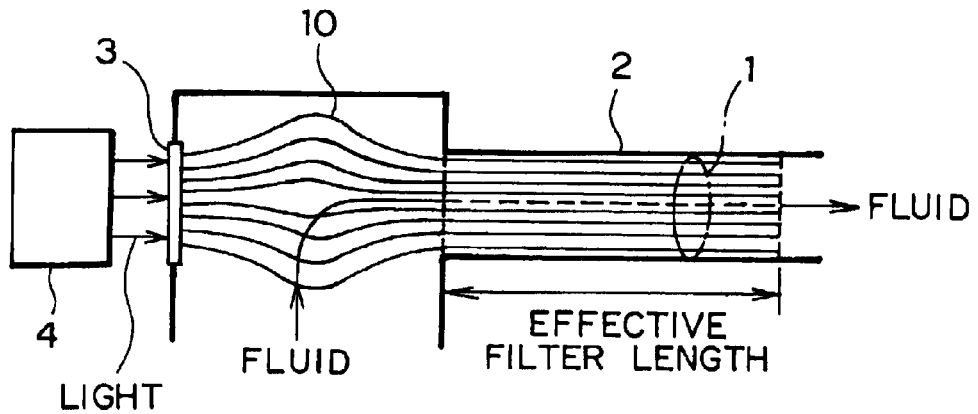

Referring to FIGS. 8A, 8B, and 8C, the filter assembly formed by photocatalyst fibers may have different structures.

In the foregoing embodiments, the filter assemblies have been formed over the full length of each photocatalyst fiber 10. However, the filter assembly may be formed by the use of only a part of each fiber 10. In this case, the remaining part of the fiber 10 may be used, for example, to form a fluid introducing section as will later be described.

In FIGS. 8A, 8B, and 8C, the photocatalyst fiber bundle 1 has a dense portion and a sparse portion in the longitudinal direction. In the dense portion and the sparse portion, the photocatalyst fibers 10 are densely and sparsely arranged, respectively. The dense portion forms the fiber assembly while the sparse portion serves as a fluid introducing section communicating with the end face of the filter assembly.

Referring to FIG. 8A, the fiber bundle 1 has a pair of sparse portions formed at its both ends where the fibers 10 are expanded into a horn shape to form a passage through which the object fluid can freely flow in and flow out. One end of each fiber 10 of the horn shape is extended to the light introducing window 3 so that the light from the light source 4 is easily introduced into the fibers 10.

In this case, each fiber 10 may have a photocatalyst layer formed only in the dense portion of the fiber bundle 1 which forms the filter assembly.

Referring to FIG. 8B, a single sparse portion where the fibers 10 are expanded into a horn shape is formed at one end of the fiber bundle 1 on a fluid inlet side.

Referring to FIG. 8C, a single sparse portion where the fibers 10 are expanded in a rounded shape is formed at a part of the fiber bundle 1 to form a passage through which the fluid can freely flows in and out.

The structures shown in FIGS. 8A, 8B, and 8C, permit the fluid to more smoothly flow into and out of the fiber bundle 1, which constitutes the filter assembly.

When the light is introduced in a direction other than the longitudinal direction of the filter assembly, a light introducing section can be formed to be continuous with the fluid introducing section or the filter assembly. The light introducing section can be formed by bending the fibers 10 at a predetermined angle. However, it is preferable to adopt an optical fiber structure in order to prevent most of the introduced light from leaking before reaching the filter assembly.

Figure 9A:
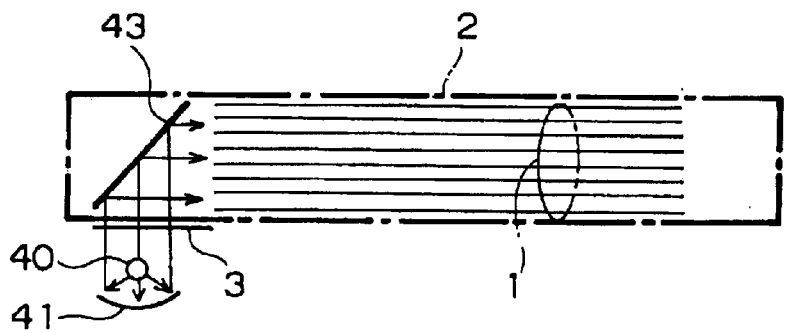
FIGS. 9A–9C are schematic views for describing various arrangements of the photocatalyst fiber bundle and a light source.
Figure 9B:
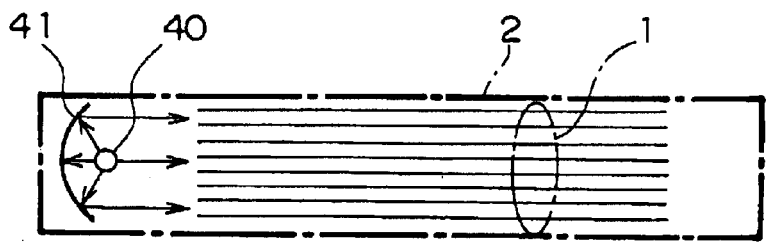
Figure 9C:
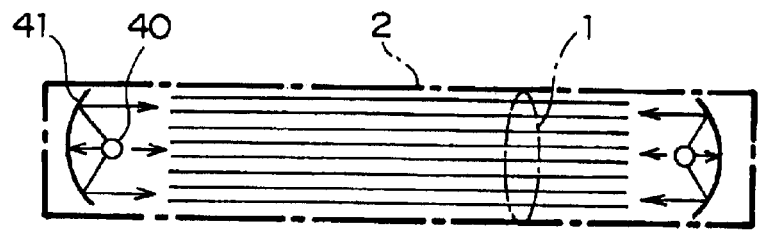

Referring to FIGS. 9A, 9B, and 9C, description will be made about various arrangements of the photocatalyst fiber bundle and the dot-type light source.

Referring to FIG. 9A, a light source 40, which may be operable as a point light source is disposed outside the casing 2. In this case, the light from the light source 40 is converged in a predetermined direction by a light converging reflection mirror 41 and then introduced into the casing 2 through the light introducing window 3. Thereafter, the light is deflected at a right angle by the reflection mirror 41 in the casing 2 to be guided to the one end face of the optical fiber bundle 1.

Referring to FIGS. 9B and 9C, the light source 40 is arranged inside the casing 2. In FIG. 9B, the light is introduced from one end of the photocatalyst fiber bundle 1. In FIG. 9C, the light is introduced from the both ends of the photocatalyst fiber bundle 1.

Figure 10:
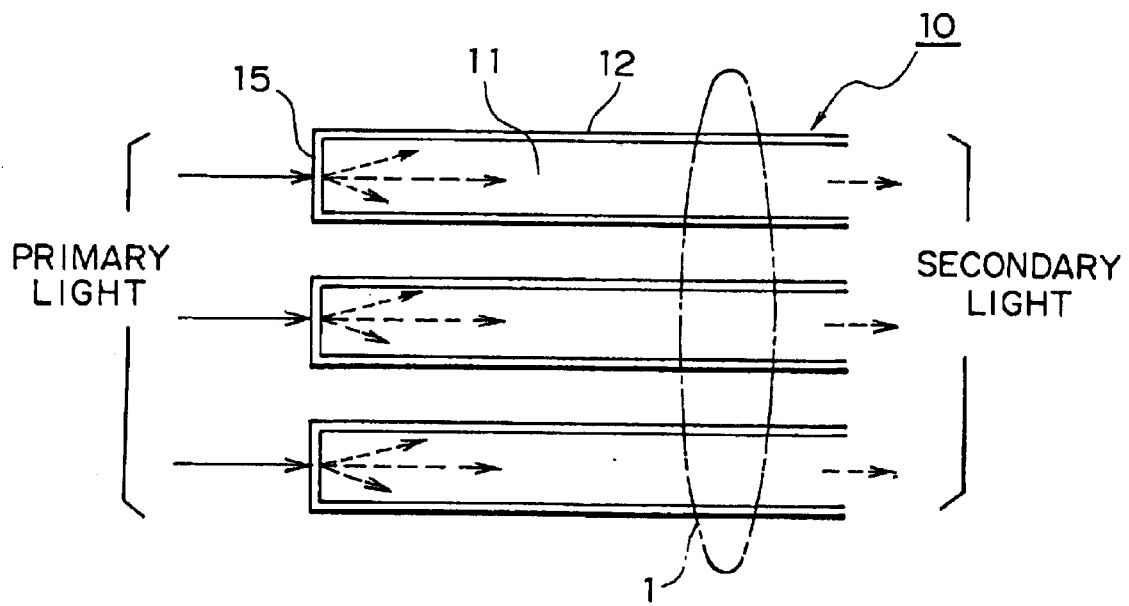
FIG. 10 is an enlarged sectional view showing a further modification in shape of the end face of the photocatalyst fiber.

Referring to FIG. 10, description will be made of a further modification in shape of the end face of the photocatalyst fiber.

As shown in FIG. 10, the light is indirectly introduced into the photocatalyst fibers 10 through a fluorescent surface 15 formed at a light introducing end of each of the photocatalyst fibers 10. The fluorescent surface 15 is supplied with primary light irradiated onto the one surface of the photocatalyst fiber 10. Excited by the primary light, the fluorescent surface 15 emits secondary light.

The wavelength of the secondary light emitted from the fluorescent surface 15 depends on the material of the fluorescent surface. If a wavelength band optimum to the photocatalytic reaction of the photocatalyst fibers 10 is matched with that of the secondary light emitted from the fluorescent surface 15, it is possible to improve the efficiency of the photocatalytic reaction.

As described above, in the first aspect of this invention, the light-leakage type photocatalyst fibers are bundled to thereby form the filter assembly having an enormous number of the minute gaps providing fluid communication paths or passageways in the longitudinal direction of the photocatalyst fibers. The light is incident to each of the photocatalyst fibers constituting the filter assembly. On the other hand, the object fluid is introduced from the one end face of the filter assembly to pass through the gaps among the photocatalyst fibers in the longitudinal direction thereof. With this structure, the object fluid can be made to pass through the photocatalyst fiber bundle along the longitudinal direction thereof. Furthermore, the flow rate distribution of the fluid passing through the fiber bundle can be rendered uniform.

From this fact, it is readily understood that the object fluid is contacted with the light leaked from the fibers over a very long distance and causes a photochemical reaction to occur between the object fluid and the leaked light (ultraviolet rays). This shows that the toxic substance, such as acetaldehyde, can be effectively removed from the object fluid, such as an air. Practically, it has been confirmed by the inventors' experimental studies that the acetaldehyde of 20 ppm was completely removed by the filter from the air by irradiating ultraviolet rays of 10 mWcm$^{-2}$ for a time interval of, about 400 minutes to the air caused to flow at a flow rate of $25 \times 10^{-3}$ min$^{-1}$.

Accordingly, it is possible to achieve the object, i.e., to simultaneously satisfy the contradictory demands for assuring the effective filter length which is sufficiently long, for reducing the pressure loss in the filter, and for increasing the filter capacity by improving the efficiency of use of the photocatalyst fibers.

In the second aspect of this invention which defines a more specific form of the first aspect of this invention, the fluid reservoirs are formed in front of the end faces of the filter assembly. With this structure, it is possible to achieve uniform pressure distribution of the object fluid at the end faces of the photocatalyst fiber bundle forming the filter assembly. Therefore, the flow rate distribution within the fiber bundle can be rendered more uniform.

In the third aspect of this invention that may be defined as a more specific form of the first or the second aspects of this invention, the light-leakage type photocatalyst fibers are bundled with the granular spacers interposed between every adjacent ones of the fibers. With this arrangement, the minute gaps can be reliably formed in the photocatalyst fiber bundle to have a size corresponding to that of the granular spacers.

In the fourth aspect of this invention that may be defined as a more specific form of any one of the first through the third aspects of this invention, the filter assembly is divided by the partition wall extending in the longitudinal direction of the photocatalyst fibers to form a plurality of the filter paths. The object fluid successively passes through these filter paths which form the cascade channel in combination. With this structure, the effective filter length can be remarkably increased.

In the fifth aspect of this invention that may be defined as a more specific form of any one of the first through the fourth aspects of this invention, the photocatalyst fiber bundle has the dense portion and the sparse portion formed at a part and the other part in the longitudinal direction to serve as the filter assembly and the fluid introducing section communicating with the end face of the filter assembly, respectively. With this structure, the fluid is allowed to more smoothly flow into and out of the fiber bundle which constitutes the filter assembly.

In the sixth aspect of this invention that may be defined as a more specific form of any one of the first through the fifth aspects of this invention, the end faces of the light-leakage type photocatalyst fiber bundle, which forms the filter assembly, are inclined with respect to the longitudinal direction of the fiber bundle. With this structure, the end face of the fiber bundle can be increased in surface area to thereby increase both of the light incident area over which the light from the light source is incident and the fluid introducing area through which the object fluid is introduced. It is therefore possible to improve the efficiency of the photocatalytic action and to reduce the pressure loss of the object fluid.

In the seventh aspect of this invention that may be defined a more specific form of any one of the first through the sixth aspects of this invention, the traveling direction of the object fluid through the photocatalyst fiber bundle is perpendicular to the light introducing direction in which the light is incident to the photocatalyst fibers. With this structure, it is possible to prevent the intervention of the light source in the flow path of the object fluid, so that the passageway resistance can be reduced.

In the eighth aspect of this invention that may be defined as a more specific form of any one of the first through the seventh aspects of this invention, the traveling direction of the object fluid through the photocatalyst fiber bundle forming the filter assembly is coincident with the light introducing direction in which the light is incident to the photocatalyst fibers. With this structure, the filter can be made compact and slender in its profile. In addition, piping for charging and discharging the object fluid can be simply arranged along the common axis.

In the ninth aspect of this invention that may be defined as a more specific form of any one of the first through the eighth aspects of this invention, the fluorescent surface for emitting the secondary light is formed at the light introducing end of each of the photocatalyst fibers. With this structure, the wavelength of the light introduced into the photocatalyst fibers can be controlled so as to increase the efficiency of the photocatalytic reaction.

In the tenth aspect of this invention that may be defined as a more specific form of any one of the first through the eighth aspects of this invention, the antireflection layer is formed on the end face of the photocatalyst fibers at the light introducing end. With this structure, the efficiency of light incidence to the photocatalytic action.

While the present invention has been described in detail in conjunction with the several preferred embodiments thereof, the present invention is not limited to the foregoing description but can be modified in various manners without departing from the scope of the invention set forth in appended claims.

As apparent from the foregoing description, according to the present invention, the light-leakage type photocatalyst fibers are bundled to thereby form the filter assembly having an enormous number of the minute apertures providing fluid communication in the longitudinal direction of the photocatalyst fibers. The light is incident to the photocatalyst fibers constituting the filter assembly while the object fluid is introduced from the end face of the filter assembly to pass through the gap between every adjacent ones of the photocatalyst fibers in the longitudinal direction thereof. With this structure, it is possible to achieve the object, i.e., to simultaneously satisfy the contradictory demands for assuring the effective filter length which is sufficiently long, for reducing the pressure loss in the filter, and for increasing the filter capacity by improving the efficiency of use of the photocatalyst fibers.

What is claimed is:

1. A light-leakage type photocatalyst filter, comprising:
    a photocatalyst fiber bundle which is formed by longitudinally bundling a plurality of photoctalyst fibers, each composed of a core portion of a photoconductor and a surface layer containing a photocatalyst, and having gaps which are left among the photocatalyst fibers and which provide passages for an object fluid;
    a casing which includes an intermediate cylindrical portion for accommodating the photocatalyst fiber bundle;
    an inflow port and an outflow port for the object fluid, each of which is formed in the vicinity of a respective side end of the casing; and a light source for introducing light beams onto at least one end face of the photocatalyst fiber bundle;

the casing further comprising:

a light introducing window which is composed of a material transparent to the light beams and which guides the light beams onto the at least one end face of the photocalyst fiber bundle; and a reservoir which is located on at least one end side of the casing adjacent to the at least one end face of the photocatalyst fiber bundle and which is coupled to the light introducing window to make pressure distribution of the object fluid uniform on the at least one end face of the photocatalyst fiber bundle.

2. A light-leakage type photocatalyst filter as claimed in claim 1, comprising granular spacers interposed among adjacent ones of the photocatalyst fibers to provide the gaps.

3. A light-leakage type photocatalyst filter, comprising:

a photocatalyst fiber bundle which is formed by longitudinally bundling a plurality of photoctalyst fibers, each composed of a core portion of a photoconductor and a surface layer containing a photocatalyst, and having gaps which are left among the photocatalyst fibers and which provide passages for an object fluid;

a casing which includes an intermediate cylindrical portion for accommodating the photocatalyst fiber bundle;

an inflow port and an outflow port for the object fluid, each of which is formed in the vicinity of respective side ends of the casing; and at least first and second light sources, each source for introducing light beams onto respective end faces of the photocatalyst fibers;

the casing further comprising:

a plurality of light introducing windows, each composed of a material transparent to the light beams and operative to guide the light beams onto respective end faces of the photocalyst fiber bundle; and at least first and second reservoirs which are located on respective sides of the casing adjacent to respective end faces of the photocatalyst fiber bundle and which are coupled to the light introducing windows, respectively, to make pressure distribution of the object fluid uniform on both end faces of the photocatalyst fiber bundle.

4. A light-leakage type photocatalyst filter as claimed in claim 3, comprising granular spacers interposed among adjacent ones of the photocatalyst fibers to provide the gaps.

5. A light-leakage type photocatalyst filter, comprising:

a photocatalyst fiber bundle which is formed by longitudinally bundling a plurality of photocatalyst fibers, each composed of a core portion of a photoconductor and a surface layer containing a photocatalyst, and having gaps which are left among the photocatalyst fibers and which provide passages for an object fluid;

a casing which includes an intermediate cylindrical portion for accommodating the photocatalyst fiber bundle and for surrounding one end of the photocatalyst fiber bundle; and a light source for introducing light beams onto a first end face of the photocatalyst fiber bundle;

the light-leakage type photocatalyst filter further comprising:

at least one partition wall extended along a longitudinal direction of the photocatalyst fibers so as to divide the photocatalyst fibers; and an inflow port and an outflow port for the object fluid, each port being located on a second end face side of the photocatalyst fiber bundle and being separated from the other port by the partition wall;

the casing further comprising:

a light introducing window of a transparent material which is located on the one end side of the casing adjacent to the one end face of the photocatalyst fiber bundle and which guides the light beams onto the one end face of the photocalyst fiber bundle; and a reservoir which is located on the one end side of the casing adjacent to the one end face of the photocatalyst fiber bundle and which is coupled to the light introducing window to make pressure distribution of the object fluid uniform on the one end face of the photocatalyst fiber bundle.

6. A light-leakage type photocatalyst filter as claimed in claim 5, comprising granular spacers interposed among adjacent ones of the photocatalyst fibers to provide the gaps.

* * * * *